US008126538B2

(12) United States Patent
Shuros et al.

(10) Patent No.: US 8,126,538 B2
(45) Date of Patent: Feb. 28, 2012

(54) METHOD AND APPARATUS FOR INTRODUCING ENDOLYMPHATIC INSTRUMENTATION

(75) Inventors: Allan C. Shuros, St. Paul, MN (US); Randy Westlund, River Falls, WI (US); M. Jason Brooke, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 447 days.

(21) Appl. No.: 11/422,423

(22) Filed: Jun. 6, 2006

(65) Prior Publication Data

US 2008/0009719 A1      Jan. 10, 2008

(51) Int. Cl.
*A61B 5/05* (2006.01)
(52) U.S. Cl. .................................. 600/427; 600/407
(58) Field of Classification Search .............. 607/17, 607/18; 600/427
See application file for complete search history.

(56) References Cited

U.S. PATENT DOCUMENTS 3,814,080 A * 6/1974 Norman ............... 600/431
(Continued)

FOREIGN PATENT DOCUMENTS

EP       1504778 A2    2/2005
(Continued)

OTHER PUBLICATIONS

"PCT Application No. PCT/US2007/068617, International Search Report mailed Mar. 10, 2008", 4 pgs.
(Continued)

*Primary Examiner* — Tse Chen
*Assistant Examiner* — Peter Luong
(74) *Attorney, Agent, or Firm* — Schwegman, Lundberg & Woessner, P.A.

(57) ABSTRACT

Described herein are a method and apparatus for introducing instrumentation into the lymphatic system that can be used for physiological monitoring and/or delivery of therapy. Such instrumentation, for example, may include one or more sensors for measuring physiological variables and/or one or more instruments for delivering therapy that is adapted to be disposed within a lymphatic vessel.

19 Claims, 5 Drawing Sheets

U.S. PATENT DOCUMENTS

| | | | |
|---|---|---|---|
| 3,916,875 A * | 11/1975 | Toch | 600/431 |
| 4,650,467 A | 3/1987 | Bonello et al. | |
| 4,792,330 A * | 12/1988 | Lazarus et al. | 604/174 |
| 4,909,787 A | 3/1990 | Danforth | |
| 4,957,484 A * | 9/1990 | Murtfeldt | 604/540 |
| 5,112,303 A | 5/1992 | Pudenz et al. | |
| 5,284,153 A * | 2/1994 | Raymond et al. | 600/554 |
| 5,305,745 A | 4/1994 | Zacouto | |
| 5,333,609 A | 8/1994 | Bedingham et al. | |
| 5,387,231 A | 2/1995 | Sporer | |
| 5,391,143 A * | 2/1995 | Kensey | 604/5.03 |
| 5,423,872 A | 6/1995 | Cigaina | |
| 5,500,005 A | 3/1996 | Strandberg et al. | |
| 5,596,988 A | 1/1997 | Markle et al. | |
| 5,655,548 A * | 8/1997 | Nelson et al. | 128/898 |
| 5,658,318 A | 8/1997 | Stroetmann et al. | |
| 5,817,138 A | 10/1998 | Suzuki | |
| 5,865,744 A | 2/1999 | Lemelson | |
| 5,891,084 A | 4/1999 | Lee | |
| 6,024,704 A | 2/2000 | Meador et al. | |
| 6,077,227 A | 6/2000 | Miesel | |
| 6,106,477 A | 8/2000 | Miesel et al. | |
| 6,115,637 A | 9/2000 | Lennox et al. | |
| 6,238,423 B1 | 5/2001 | Bardy | |
| 6,272,370 B1 * | 8/2001 | Gillies et al. | 600/411 |
| 6,292,695 B1 | 9/2001 | Webster, Jr. et al. | |
| 6,321,109 B2 * | 11/2001 | Ben-Haim et al. | 600/424 |
| 6,347,247 B1 | 2/2002 | Dev et al. | |
| 6,368,274 B1 | 4/2002 | Van Antwerp et al. | |
| 6,370,417 B1 * | 4/2002 | Horbaschek et al. | 600/424 |
| 6,475,223 B1 * | 11/2002 | Werp et al. | 606/108 |
| 6,535,764 B2 * | 3/2003 | Imran et al. | 607/40 |
| 6,542,776 B1 | 4/2003 | Gordon et al. | |
| 6,584,362 B1 | 6/2003 | Scheiner et al. | |
| 6,587,719 B1 | 7/2003 | Barrett et al. | |
| 6,606,523 B1 | 8/2003 | Jenkins | |
| 6,609,025 B2 | 8/2003 | Barrett et al. | |
| 6,611,715 B1 | 8/2003 | Boveja | |
| 6,615,084 B1 | 9/2003 | Cigaina | |
| 6,629,534 B1 | 10/2003 | Fredrick et al. | |
| 6,678,557 B1 | 1/2004 | Tumey | |
| 6,684,104 B2 | 1/2004 | Gordon et al. | |
| 6,741,882 B2 * | 5/2004 | Schaffter et al. | 600/424 |
| 6,826,428 B1 | 11/2004 | Chen et al. | |
| 6,835,194 B2 | 12/2004 | Johnson et al. | |
| 6,879,859 B1 | 4/2005 | Boveja | |
| 6,889,076 B2 | 5/2005 | Cigaina | |
| 6,893,429 B2 | 5/2005 | Petersen | |
| 6,895,278 B1 | 5/2005 | Gordon | |
| 6,918,873 B1 | 7/2005 | Millar et al. | |
| 6,950,707 B2 | 9/2005 | Whitehurst | |
| 6,970,741 B1 | 11/2005 | Whitehurst | |
| 6,974,448 B2 | 12/2005 | Petersen | |
| 7,295,877 B2 | 11/2007 | Govari | |
| 7,317,941 B2 | 1/2008 | Stomberg et al. | |
| 7,526,337 B2 | 4/2009 | Shuros et al. | |
| 7,606,622 B2 | 10/2009 | Reeve | |
| 7,616,991 B2 | 11/2009 | Mann et al. | |
| 7,734,341 B2 | 6/2010 | Shuros | |
| 7,774,055 B1 | 8/2010 | Min | |
| 7,894,906 B2 | 2/2011 | Shuros | |
| 2001/0037061 A1 | 11/2001 | Eckmiller et al. | |
| 2001/0041870 A1 * | 11/2001 | Gillis et al. | 604/164.09 |
| 2002/0016615 A1 | 2/2002 | Dev et al. | |
| 2002/0029037 A1 * | 3/2002 | Kim | 606/41 |
| 2002/0072780 A1 | 6/2002 | Foley | |
| 2002/0087192 A1 | 7/2002 | Barrett et al. | |
| 2002/0123674 A1 * | 9/2002 | Plicchi et al. | 600/300 |
| 2002/0156462 A1 | 10/2002 | Stultz | |
| 2002/0188253 A1 * | 12/2002 | Gordon et al. | 604/101.03 |
| 2003/0036773 A1 | 2/2003 | Whitehurst et al. | |
| 2003/0055463 A1 | 3/2003 | Gordon et al. | |
| 2003/0078623 A1 | 4/2003 | Weinberg et al. | |
| 2003/0105506 A1 * | 6/2003 | Krishnan et al. | 607/126 |
| 2003/0113303 A1 | 6/2003 | Schwartz | |
| 2003/0114895 A1 | 6/2003 | Gordon et al. | |
| 2003/0144708 A1 | 7/2003 | Starkebaum | |
| 2003/0204185 A1 | 10/2003 | Sherman et al. | |
| 2004/0015193 A1 | 1/2004 | Lamson et al. | |
| 2004/0015201 A1 | 1/2004 | Greenstein | |
| 2004/0024428 A1 | 2/2004 | Barrett et al. | |
| 2004/0039427 A1 | 2/2004 | Barrett et al. | |
| 2004/0088022 A1 | 5/2004 | Chen | |
| 2004/0102804 A1 * | 5/2004 | Chin | 606/190 |
| 2004/0106953 A1 * | 6/2004 | Yomtov et al. | 607/3 |
| 2004/0147976 A1 | 7/2004 | Gordon et al. | |
| 2004/0162595 A1 | 8/2004 | Foley | |
| 2004/0172080 A1 | 9/2004 | Stadler et al. | |
| 2004/0172102 A1 | 9/2004 | Leysieffer | |
| 2004/0210118 A1 * | 10/2004 | Letort | 600/339 |
| 2004/0230255 A1 | 11/2004 | Dobak, III | |
| 2005/0033376 A1 | 2/2005 | Whitehurst | |
| 2005/0043675 A1 * | 2/2005 | Pastore et al. | 604/67 |
| 2005/0043765 A1 | 2/2005 | Williams et al. | |
| 2005/0043894 A1 | 2/2005 | Fernandez | |
| 2005/0049472 A1 | 3/2005 | Manda | |
| 2005/0065575 A1 | 3/2005 | Dobak | |
| 2005/0070974 A1 | 3/2005 | Knudson et al. | |
| 2005/0075678 A1 | 4/2005 | Faul | |
| 2005/0075701 A1 | 4/2005 | Shafer | |
| 2005/0075702 A1 | 4/2005 | Shafer | |
| 2005/0080346 A1 * | 4/2005 | Gianchandani et al. | 600/486 |
| 2005/0080462 A1 | 4/2005 | Jenkins et al. | |
| 2005/0090873 A1 | 4/2005 | Imran | |
| 2005/0143765 A1 * | 6/2005 | Bachmann et al. | 606/157 |
| 2005/0149014 A1 * | 7/2005 | Hauck et al. | 606/41 |
| 2005/0187584 A1 | 8/2005 | Denker et al. | |
| 2005/0222637 A1 | 10/2005 | Chen | |
| 2005/0222638 A1 | 10/2005 | Foley et al. | |
| 2005/0228471 A1 | 10/2005 | Williams et al. | |
| 2005/0246006 A1 | 11/2005 | Daniels | |
| 2005/0267440 A1 | 12/2005 | Herman et al. | |
| 2005/0273060 A1 | 12/2005 | Levy et al. | |
| 2005/0288729 A1 | 12/2005 | Libbus et al. | |
| 2005/0288730 A1 | 12/2005 | Deem et al. | |
| 2006/0020333 A1 * | 1/2006 | Lashinski et al. | 623/2.11 |
| 2006/0074453 A1 * | 4/2006 | Kieval et al. | 607/9 |
| 2006/0149331 A1 | 7/2006 | Mann et al. | |
| 2006/0217779 A1 | 9/2006 | Ransbury et al. | |
| 2006/0247601 A1 | 11/2006 | Ellin et al. | |
| 2007/0021731 A1 | 1/2007 | Garibaldi et al. | |
| 2007/0027460 A1 * | 2/2007 | Case et al. | 606/151 |
| 2007/0244520 A1 | 10/2007 | Ferren et al. | |
| 2007/0255340 A1 | 11/2007 | Giftakis et al. | |
| 2007/0270675 A1 | 11/2007 | Kane et al. | |
| 2007/0282376 A1 | 12/2007 | Shuros | |
| 2007/0282380 A1 | 12/2007 | Brooke et al. | |
| 2007/0282382 A1 | 12/2007 | Shuros et al. | |
| 2007/0282386 A1 | 12/2007 | Shuros | |
| 2007/0282390 A1 | 12/2007 | Shuros | |
| 2008/0086185 A1 | 4/2008 | Amurthur et al. | |
| 2008/0097412 A1 | 4/2008 | Shuros et al. | |
| 2008/0260861 A1 | 10/2008 | Hagendoorn et al. | |
| 2009/0228059 A1 | 9/2009 | Shuros | |
| 2010/0042170 A1 | 2/2010 | Allan et al. | |
| 2010/0217346 A1 | 8/2010 | Shuros | |
| 2011/0106202 A1 | 5/2011 | Ding et al. | |

FOREIGN PATENT DOCUMENTS

| | | |
|---|---|---|
| SU | 1074527 A1 | 2/1984 |
| WO | WO-9314694 A1 | 8/1993 |
| WO | WO-03028542 A2 | 4/2003 |
| WO | WO-9314694 A1 | 8/2003 |
| WO | WO-03098177 A2 | 11/2003 |
| WO | WO 2004006795 A1 * | 1/2004 |
| WO | WO-2004032791 A2 | 4/2004 |
| WO | WO-2005089863 A1 | 9/2005 |
| WO | WO-2007067690 A2 | 6/2007 |
| WO | WO-2007146489 A2 | 12/2007 |
| WO | WO-2007146489 A3 | 12/2007 |
| WO | WO-2007146493 A1 | 12/2007 |
| WO | WO-2007146517 A2 | 12/2007 |
| WO | WO-2008030344 A2 | 3/2008 |

OTHER PUBLICATIONS

"PCT Application No. PCT/US2007/068617, Written Opinion mailed Mar. 10, 2008", 8 pgs.

"Physician's Manual—VNS Therapy tm Lead Model 302", Copyright 2003, 2004, 2005 Cyberonics, Inc., Houston, Tx,(Jul. 2005),35 pgs.

Knott, E. M., et al., "Increased lymphatic flow in the thoracic duct during manipulative intervention", *J Am Osteopath Assoc.*, 105(10), (Oct. 2005),447-56.

Pulley, M. S., et al., "Intravenous, intralesional and endolymphatic administration of lymphokines in human cancer.", *Lymphokine Res., 5 Suppl 1*, (1986), S157-63.

Gray, H., et al., "2. The Thoractic Duct", *Anatomy of the Human Body, Philadelphia: Lea & Febeiger,*, [online]. Bartleby.com 2000. Retrieved from the Internet: <URL:www.bartleby.com/107>, (1918), 3 pgs.

Sobotta, J, et al., *Atlas of Human Anatomy*, vol. III, W.B. Saunder Company, (2006), 274-275.

Yimtae, K., et al., "Connection between the inner ear and the lymphatic system", *Laryngoscope*, 111(9), (Sep. 2001), 1631-5.

"U.S. Appl. No. 11/422,414, Notice of Allowance mailed Oct. 13, 2010", 7 pgs.

"U.S. Appl. No. 11/422,414, Response filed Aug. 26, 2010 to Non Final Office Action mailed May 27, 2010", 6 pgs.

* cited by examiner

METHOD AND APPARATUS FOR INTRODUCING ENDOLYMPHATIC INSTRUMENTATION

RELATED APPLICATIONS

This application is related to co-pending application Ser. No. 11/422,414, entitled "AMELIORATION OF CHRONIC PAIN BY ENDOLYMPHATIC STIMULATION," filed Jun. 6, 2006, application Ser. No. 11/422,417, entitled "METHOD AND DEVICE FOR LYMPHATIC SYSTEM MONITORING," filed Jun. 6, 2006, application Ser. No. 11/422,418, entitled "METHOD AND APPARATUS FOR GASTROINTESTINAL STIMULATION VIA THE LYMPHATIC SYSTEM," filed Jun. 6, 2006, and application Ser. No. 11/422,421, entitled "METHOD AND APPARATUS FOR NEURAL STIMULATION VIA THE LYMPHATIC SYSTEM," filed on Jun. 6, 2006, all of which are hereby incorporated by reference.

FIELD OF THE INVENTION

This invention pertains to methods and systems for diagnosing and treating disease with implantable devices.

BACKGROUND

The lymphatic system and the cardiovascular system are closely related structures that are indirectly joined by a capillary system. The lymphatic system is important to the body's defense mechanisms by filtering out organisms that cause disease and by producing lymphocytes that attack foreign organisms and generate antibodies. It is also important for the distribution of fluids and nutrients in the body, because it drains excess fluids and protein from interstitial tissues. Fluid that seeps out of the blood vessels into the interstitial spaces of body tissues and other interstitial components are then absorbed by lymphatic capillaries to form lymph that flows back into the bloodstream through the lymphatic vessels. The terminal structures of the lymphatic vessels include the right lymphatic duct, which drains lymph fluid from the upper right quarter of the body above the diaphragm and down the midline, and the thoracic duct, located in the mediastinum of the pleural cavity which drains the rest of the body. Through the flow of blood in and out of arteries, into the veins, and through the lymph vessels and nodes, the body is able to eliminate the products of cellular breakdown and foreign body invasion.

SUMMARY

Described herein are a method and apparatus for introducing instrumentation into the lymphatic system that can be used for physiological monitoring and/or delivery of therapy. Such instrumentation, for example, may include one or more sensors for measuring physiological variables and/or one or more instruments for delivering therapy that is adapted to be disposed within a lymphatic vessel. The instrumentation may be connected to an implantable device, by means of a lead or wirelessly, that receives signals from the instrumentation and/ or controls the delivery of therapy. The implantable device may also communicate with an external system via a telemetry link. In another embodiment, the lymphatic instrumentation may be wirelessly connected to an external control device.

DETAILED DESCRIPTION

The lymphatic vessels are part of the body's circulatory system and serve as a pathway by which fluids can flow from the interstitial spaces into blood. Lymphatic vessels also communicate with lymph nodes and facilitate the body's immune function by transporting foreign antigens to the lymph nodes from the interstitial spaces. As described below, an implantable device may be configured to monitor lymphatic function and thereby detect particular conditions such as edema, inflammation, and other disease states. The device may be further configured to deliver appropriate therapy in accordance with the lymphatic monitoring. In addition, lymphatic vessels generally run alongside nerves as they course through the body, and lymph nodes and other parts of the lymphatic system are often located near nerve endings and pain receptors. This makes the lymphatic system a convenient conduit for routing a lead from an implantable pulse generator to an electrode (or connecting the electrode to pulse generator wirelessly) in order to deliver neural electrical stimulation to or sense neural activity from internal body locations. Delivering neural electrical stimulation in this manner may be used, for example, to treat pain. Nerve blocking stimulation may be delivered to nerves located near lymphatic vessels such as nerves emanating from the spine, or other internal organs.

Figure 1:
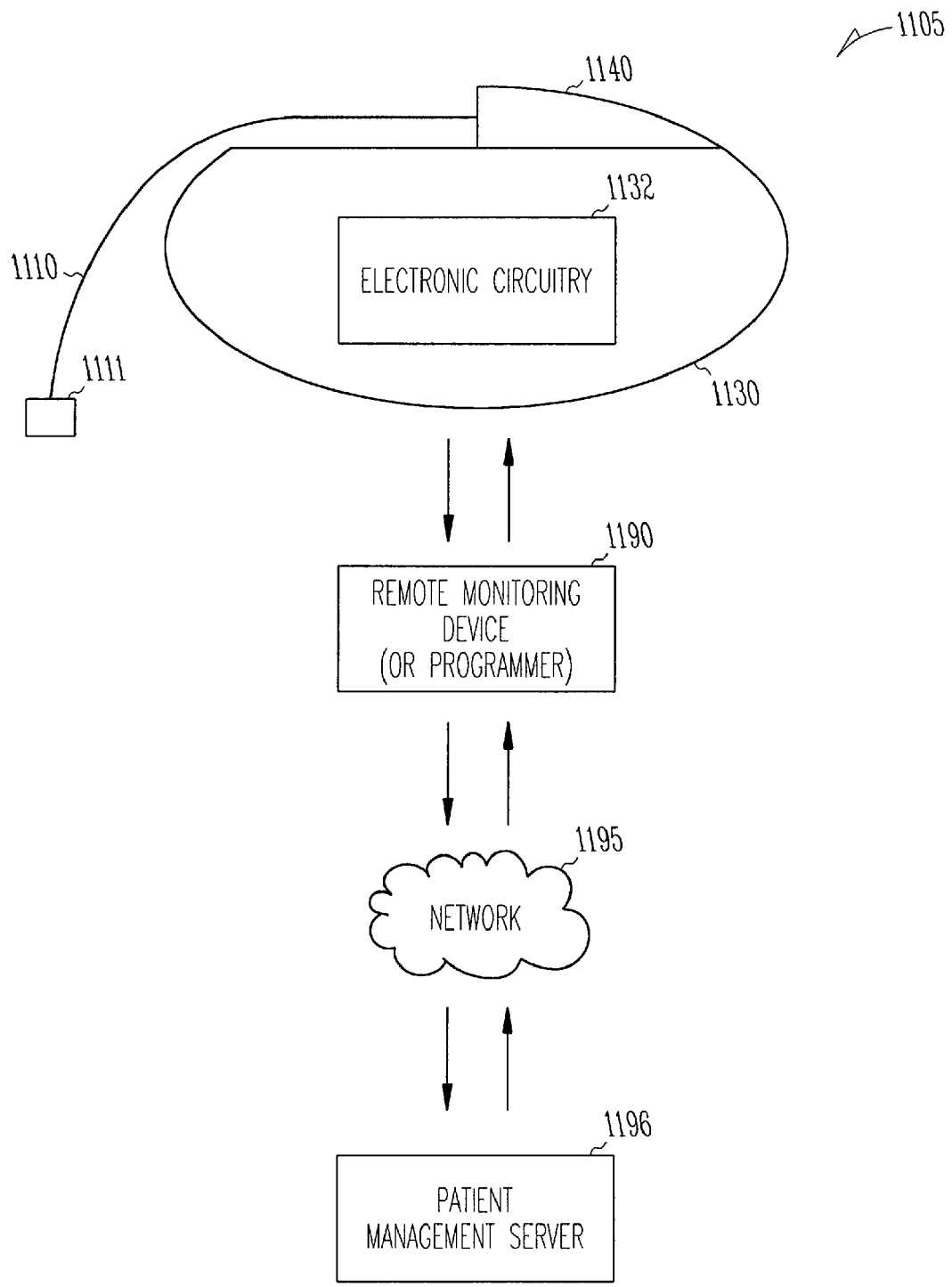
FIG. 1 shows an exemplary system for physiological monitoring and/or therapy delivery via the lymphatic system.

FIG. 1 shows an exemplary system for physiological monitoring and/or therapy delivery via the lymphatic system which includes an implantable control device and a lymphatic instrument adapted for disposition in a lymphatic vessel. An implantable control device 1105 includes a hermetically sealed housing 1130 that may be placed subcutaneously or submuscularly in a patient's chest, similar to a cardiac pacemaker, or other convenient location. The housing 1130 may be formed from a conductive metal, such as titanium, and may additionally serve as an electrode for delivering electrical stimulation. Contained within the housing 1130 is the electronic circuitry 1132 for providing the functionality to the system as described herein which may include a power supply, monitoring circuitry, therapy circuitry, and a programmable electronic controller for controlling the operation of the system. A header 1140, which may be formed of an insulating material, is mounted on the housing 1130 for receiving one or more leads 1110 which are electrically connected to the circuitry within the housing. At the distal end of a lead 1110 is a lymphatic instrument 1111 that may be either a sensing or therapy delivering instrument. A lymphatic instrument is adapted for disposition in a lymphatic vessel and may thus be referred to as endolymphatic instrumentation. In another embodiment, rather than being connected to the circuitry of the implantable control device by a lead, the lymphatic instrument is incorporated into a satellite unit that communicates wirelessly with the control device in order to receive commands and/or transmit data.

Figure 2:
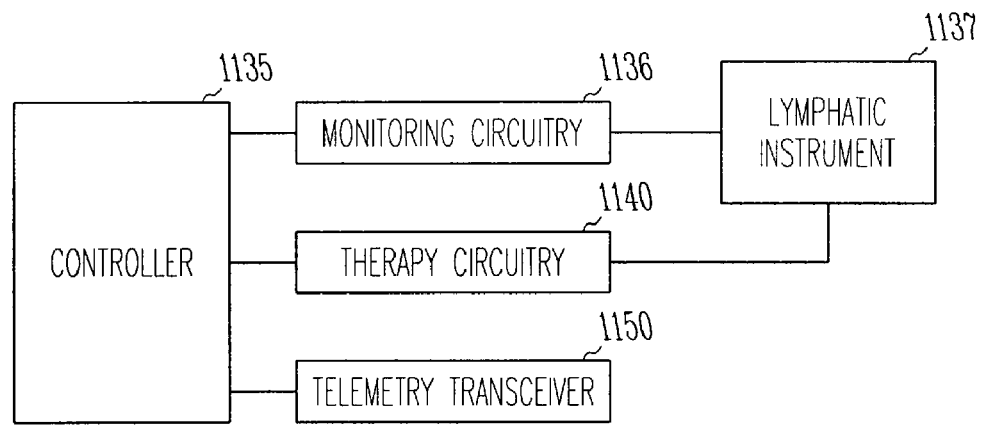
FIG. 2 illustrates exemplary components of the electronic circuitry 132 depicted in FIG. 1.

FIG. 2 illustrates exemplary components of the electronic circuitry 1132 depicted in FIG. 1. A controller 1135 is provided which may be made up of discrete circuit elements but is preferably a processing element such as a microprocessor together with associated memory for program and data storage which may be programmed to perform algorithms for delivering therapy. (As the terms are used herein, "circuitry" and "controller" may refer either to a programmed processor or to dedicated hardware components configured to perform a particular task.) The controller is interfaced to monitoring circuitry 1136 from which it receives data generated by one or more lymphatic instruments 1137. The monitoring circuitry may include, for example, circuitry for amplification, filtering, and/or analog-to-digital conversion of voltages generated by a lymphatic sensor. In the illustrated embodiment, the controller 1135 is also interfaced to therapy circuitry 1140 in order to control the delivery of therapy by the device in response to conditions sensed by the monitoring circuitry. The therapy circuitry 1140 may include circuitry for delivery one or more therapy modalities such as electro-stimulation and drug therapy. The lymphatic instrument 1137 in the former case is an electrode, while in the latter case it includes a drug delivery device actuated by the therapy circuitry of the implantable control device that may be used to deliver medication in response to detection of particular conditions. Such medications could include anti-inflammatory drugs, cancer chemotherapeutic agents, diuretics, cardiac drugs, pain relief medication, glucagon, insulin or other pharmacologic therapy.

Also interfaced to the controller in FIG. 2 is a telemetry transceiver 1150 capable of communicating with an external programmer or a remote monitoring device 1190 as shown in FIG. 1. An external programmer wirelessly communicates with the device 1105 and enables a clinician to receive data and modify the programming of the controller. A remote monitoring device similarly communicates with the device 1105 and is further interfaced to a network 1195 (e.g., an internet connection) for communicating with a patient management server 1196 that allows clinical personnel at remote locations to receive data from the remote monitoring device as well as issue commands. The controller may be programmed such that when particular conditions are detected by the monitoring circuitry (such as when a measured parameter exceeds or falls below a specified limit value), the device transmits an alarm message to the remote monitoring device and to the patient management server to alert clinical personnel.

Figure 3:
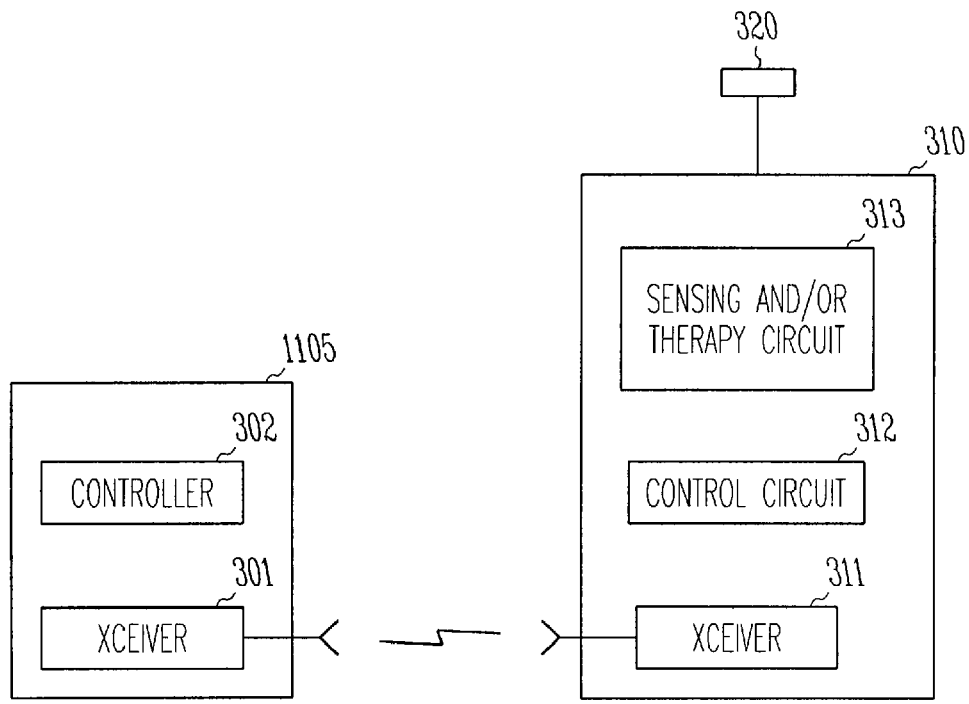
FIG. 3 illustrates an embodiment of system where the lead connecting the lymphatic instrument to the implantable control device is replaced by a wireless link.

FIG. 3 illustrates an embodiment of system where the lead connecting the lymphatic instrument to the implantable control device is replaced by a wireless link. The wireless link may be, for example, a radio-frequency (RF) link or an acoustic link. The lymphatic instrument 320 in this embodiment is incorporated into a satellite unit 310. The satellite unit 310 is an integrated assembly adapted for implantation into a lymphatic vessel either surgically or by means of a catheter as described below and includes a housing containing a battery and circuitry for sensing and/or delivering therapy. The control device 1105 in this embodiment may be either an implantable or an external device and includes a wireless telemetry transceiver for communicating with the satellite unit, illustrated in this embodiment as a transceiver 301 (e.g., either an RF transceiver or an acoustic transducer) interfaced to the controller 302 for transmitting commands and/or receiving data. The satellite unit 310 similarly includes a wireless transceiver 311 interfaced to control circuitry 312 for receiving the commands and/or transmitting data. The control circuitry 312 translates the received commands and causes therapy circuitry 313 to actuate a therapy modality such as electro-stimulation or chemical delivery.

Figure 4:
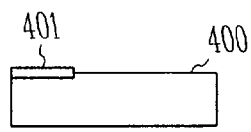
FIG. 4 illustrates a stent that incorporates a lymphatic instrument.

As aforesaid, the lymphatic instrument may be connected to the implantable control device either wirelessly or via a lead. In the latter case, the lymphatic instrument is incorporated into the lead. The lymphatic instrument may also be incorporated into a stent that is expanded in the lymphatic vessel in order to maintain patency of the vessel. Such a stent may incorporate either a lymphatic instrument attached to a lead or a leadless lymphatic instrument that communicates wirelessly with implantable control device as described above. FIG. 4 illustrates a stent 400 that incorporates a lymphatic instrument 401, where the lymphatic instrument is attached to a wall of the stent in a manner that does not impede lymphatic flow.

In an embodiment where the lymphatic instrument 1137 (FIG. 2) is a sensor, it may be a flow or pressure sensor for sensing conditions within a lymphatic vessel that indicate edema may be present. Edema occurs when the lymphatic vessels are overwhelmed with fluid due to, for example, elevated venous pressure caused by heart failure and renal compensation thereof, kidney disease, or liver disease. Under such conditions, the pressure and/or flow of lymph within the lymphatic vessels may be increased. The system may be configured to deliver an appropriate medication when edema is detected (e.g., an ACE inhibitor or angiotensin receptor blocker.) The composition of lymphatic fluid may also be monitored to determine if particular clinical states exist. For example, the concentration of cytokines and immunoglobulins may be used to assess certain autoimmune diseases and cancer. When the concentration of such substances reaches a particular level, the device may then be configured to deliver an appropriate medication. In this embodiment, the lymphatic sensor is a chemo-sensor designed to generate a voltage proportional to the concentration of a particular chemical species. The chemo-sensor may be used to provide to the controller an indication or measurement of the concentration of a particular molecule in the lymphatic fluid that is of interest, referred to as a marker. Examples of markers whose concentrations may be of diagnostic value include immunoglobulins, cytokines, or specific ions or proteins that could be used to characterize a particular disease state. Such chemo-sensors may use immobilized antibodies (Ab) with binding affinities specific for the different marker antigens (Ag). Upon formation of an Ab-Ag complex between the antibody and the marker, the chemo-sensor may produce an electrical signal by, for example, incorporating a piezoelectric transducer that responds to mechanical stresses induced by the Ab-Ag complex or a transducer that responds to potential changes resulting from the Ab-Ag complex.

In an embodiment where the lymphatic instrument 1137 (FIG. 2) is for delivering therapy the instrument may be an electro-stimulator for stimulating nerves, cardiac muscle, smooth muscle, or skeletal muscle. The lymphatic instrument could also be a mechanical stimulator for neural/muscle stimulation, an ultrasonic stimulator, or a piezoelectric modulated stimulator. In another embodiment, the instrument is a catheter for delivery of media such as immunomodulation agents, cancer therapy agents, anti-inflammatory agents, steroids, cells, genes, hormones, or other pharmacological agents. The media delivering instrument may also deliver agents for repair of damaged lymphatic vessels such as a material-based stent to seal holes but preserve patency. In other embodiments, the instrument is adapted for photo-electric stimulation or fluid modulation therapy.

Figure 5:
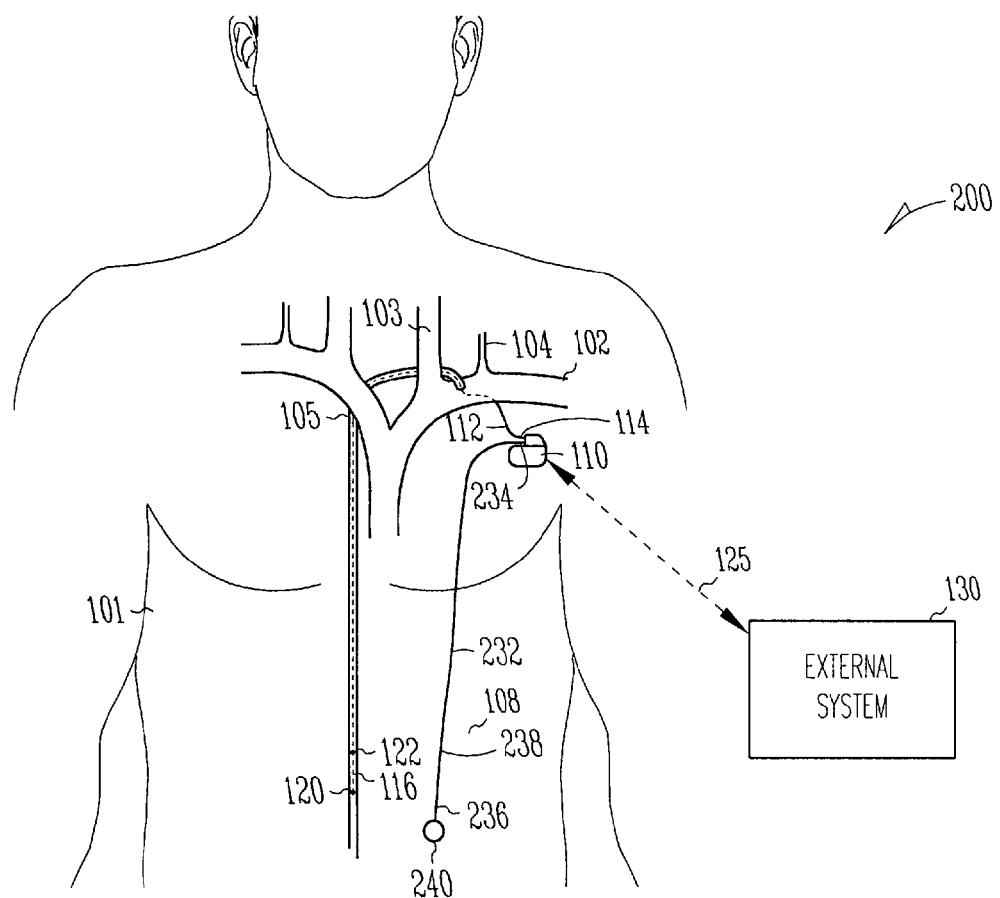
FIG. 5 shows an exemplary physical placement of an implantable control device and endolymphatic instrumentation.

FIG. 5 shows an exemplary physical placement within a body 101 of a system 200 for physiological monitoring and/or therapy delivery via the lymphatic system that includes an implantable control device 110 and lymphatic instrument(s) as described herein. In this embodiment, the implantable control device 110 is placed subcutaneously on the patient's chest or abdomen, similar to a standard cardiac pacemaker. The implantable control device 110 communicates via a telemetry link 125 with an external system 130, such as an external programmer or remote monitoring unit. External system 130 communicates with implantable device 110 and provides for access to implantable device 110 by a physician or other caregiver. In one embodiment, external system 130 is an external programmer. In another embodiment, external system 130 is a patient management system including an external device communicating with implantable device 110 via telemetry link 125, a remote device in a relatively distant location, and a telecommunication network linking the external device and the remote device. The patient management system allows access to implantable device 110 from a remote location, for purposes such as monitoring patient status and adjusting therapies. In one embodiment, telemetry link 125 is an inductive telemetry link. In another embodiment, telemetry link 125 is a far-field radio-frequency (RF) telemetry link. Telemetry link 125 provides for data transmission from implantable device 110 to external system 130. This includes, for example, transmitting real-time physiological data acquired by implantable device 110, extracting physiological data acquired by and stored in implantable device 110, extracting patient history data such as occurrences of predetermined types of pathological events and therapy deliveries recorded in implantable device 110, and/or extracting data indicating an operational status of implantable device 110 (e.g., battery status and lead impedance). Telemetry link 125 also provides for data transmission from external system 130 to implantable medical device 110. This includes, for example, programming implantable device 110 to acquire physiological data, to perform at least one self-diagnostic test (such as for a device operational status), and/or to deliver one or more therapies and/or to adjust the delivery of one or more therapies.

In certain embodiments, the implantable control device may also incorporate cardiac pacing and/or cardioversion/defibrillation functionality with leads and associated circuitry for that purpose. The implantable device may also be configured to deliver additional therapies such as cardiac resynchronization therapy (CRT), cardiac remodeling control therapy (RCT), drug therapy, cell therapy, and gene therapy. The implantable control device 110 in this embodiment is connected to one or more leads 112, each having a distal member that incorporates a lymphatic instrument. The lead 112 passes subcutaneously from the control device 110 to a point of venous access in the upper chest or neck such as the subclavian vein. As described below, the lead may be positioned within the lymphatic system using a venous approach which involves initial entry into the venous blood system. A similar technique employing a catheter may be used to implant a stent incorporating a wireless lymphatic instrument.

FIG. 5 also illustrates portions of the lymphatic and venous system including portions of thoracic duct 105, a subclavian vein 102, a left external jugular vein 103, and a left internal jugular vein 104. Thoracic duct 105 connects to subclavian vein 102 at the juncture of subclavian vein 102 and a left internal jugular vein 104. Lymphatic fluid from the lower body flows up to thoracic duct 105 and empties into subclavian vein 102 from thoracic duct 105. The thoracic duct 105 is located in the posterior mediastinal area of the body 101, which is adjacent to the heart and includes various portions of the nervous system including portions of the vagus, sympathetic, and phrenic nerves. In one embodiment, electrical stimulation of such nerves may be delivered by one or more stimulation electrodes incorporated into lead 112 and placed within thoracic duct 105. Thoracic duct 105 can also be used as a conduit for advancing one or more stimulation electrodes to a location from which electrical stimulation can be delivered to a target region of the nervous system of body 101. Electrodes incorporated into lead 112 may also be used to sense neural activity as well other physiological signals.

Lead 112 includes a proximal end 114, a distal end 116, and an elongate lead body 118 between proximal end 114 and distal end 116. Proximal end 114 is coupled to the implantable device 110. Distal end 116 includes at least one lymphatic instrument as described above. In the embodiment illustrated in FIG. 5, distal end 116 includes electrodes 120 and 122 for sensing and/or stimulation. The implantable device 110 may include a hermetically sealed conductive housing that functions as a reference electrode. The distal portion of elongate lead body 118 (a substantial portion of elongate lead body 118 coupled to distal end 116) is configured for placement in subclavian vein 102 and thoracic duct 105, such that distal end 116 is placed in thoracic duct 105. During the implantation of lead 112, distal end 116 is inserted into subclavian vein 102 through an incision, advanced in subclavian vein 102 toward thoracic duct 105, inserted into thoracic duct 105 from subclavian vein 102, and advanced in thoracic duct 105 until a predetermined location in thoracic duct 105 is reached. In one embodiment, the position of distal end 116 is adjusted by delivering test stimulation pulses and detecting evoked neural signals and/or other physiological responses. In another embodiment, lead 112 includes a fixation mechanism configured to stabilize distal end 116 in the determined position in thoracic duct 105. Also shown in the illustrated embodiment is an additional lead 232 that includes a proximal end 234, a distal end 236, and an elongate lead body 238 between proximal end 234 and distal end 236. The lead 232 may be configured for subcutaneous placement, external to thoracic duct 105. Proximal end 234 is coupled to implantable device 110, and, in this embodiment, distal end 236 includes an electrode 240 that may be used for sensing and/or stimulation or for use as a reference electrode with any of the other electrodes of the implantable device 110. Lead 232 expands the range of target regions to which stimulation pulses can be delivered from implantable device 110.

In order to implant a lead incorporating a lymphatic instrument or a wireless satellite unit into a selected location within lymphatic vessel, the lymphatic system may be visualized using lymphangiograpy. In this technique, dye is injected into the subcutaneous tissue of an extremity such as the foot, or other peripheral lymph vessel, and the lymphatic system drains the dye making the lymphatic vessels visible. A lymphatic vessel is cannulated, and radiopaque contrast is injected to illuminate major lymph vessels including the thoracic duct and its ostium into the subclavian vein. A catheter may then be guided into the thoracic duct ostium via the venous system using fluoroscopy techniques and positioned at a selected location within the lymphatic system. Initial cannulation of the lymph ostium with a guide wire or catheter may be achieved through the left or right subclavian vein, the left jugular veins, the epigastric/mammary veins or the femoral veins. In order to facilitate navigation through the lymphatic vessels and position the lymphatic instrument at a selected anatomical location, an overlapping technique may be employed whereby fluoroscopic images produced by the injected dye are used in conjunction with anatomical images of the patient produced by other modalities such as conventional x-ray, CAT scans, MRI scans, or ultrasonic scans. The fluoroscopic image may be overlaid with the anatomical image and the catheter then guided to the selected location.

To implant the lead or satellite unit, a catheter may be introduced into the venous system and from there into the thoracic duct ostium using conventional over-the-wire techniques that employ a guide wire. Alternatively, a lead having a lumen for a guide wire may be similarly introduced. The guide wire is manually or mechanically pushed and manipulated to guide its travel and upon which catheters and/or leads may be advanced. A stereotaxis technique in which external magnets or other means are used to guide the catheter may also be used to improve maneuverability and precision as well as provide increased safety. An example of this technique is described in U.S. Pat. No. 6,475,223, hereby incorporated by reference. Once the catheter is in the lymphatic system, it must also traverse valves in the lymphatic vessels whose function is to allow flow of lymphatic fluid in only one direction to the thoracic duct. As the catheter is guided through a vessel to one of these valves, the catheter may incorporate a vacuum system to open the valves. When the vacuum system is actuated, it draws negative pressure to create a pressure gradient that opens the valve. An alternative technique for opening lymphatic valves involves using a catheter incorporating a compliant balloon on its distal tip. When the catheter reaches a lymphatic valve, the balloon is inflated to mechanically dilate the vessel which opens the valve and allows a wire or the catheter to pass through. In still another technique, the catheter incorporated an electrode at its tip (which may or may not be a lymphatic instrument intended to be left in the lymphatic vessel) that is used to cause smooth muscle contraction of the lymphatic vessel. Such smooth muscle contraction can create a pressure gradient that opens the valve and allows the catheter to advance past the valve.

Figure 6:
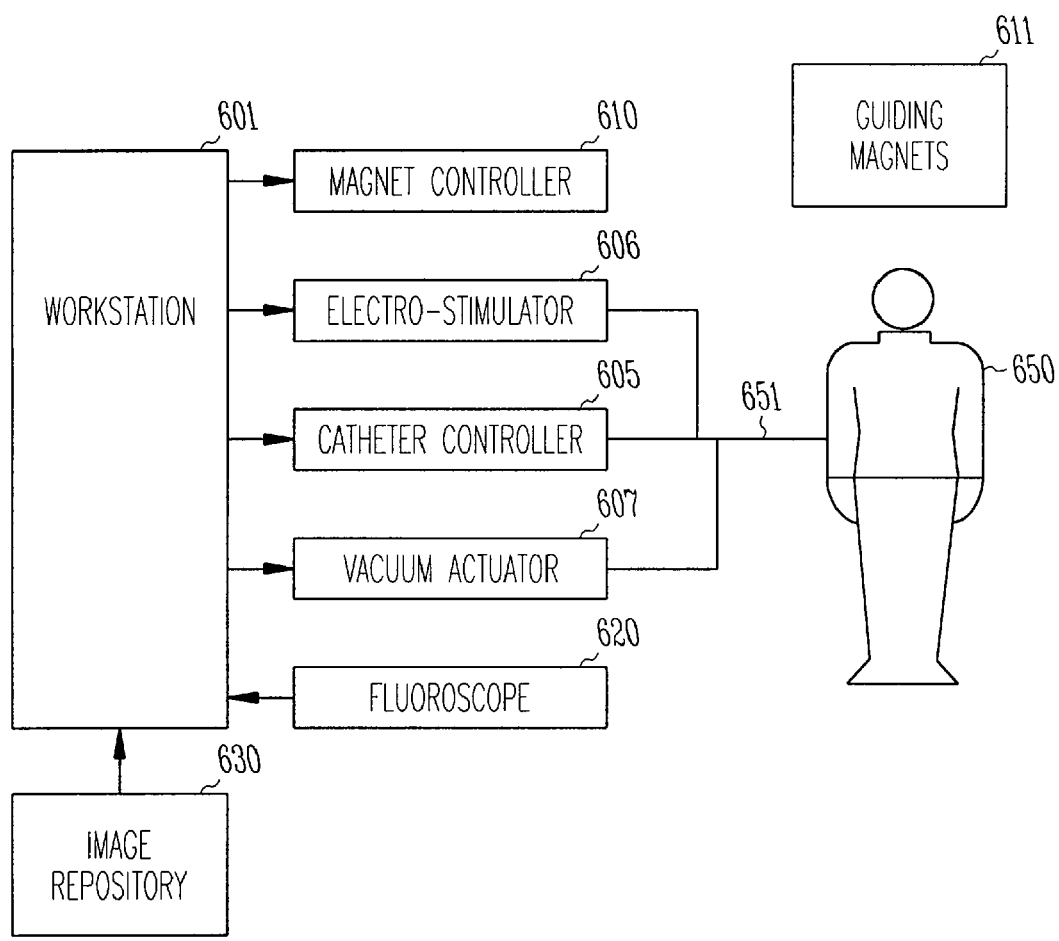
FIG. 6 shows an exemplary system for introducing endolymphatic instrumentation.

FIG. 6 shows an exemplary system for introducing endolymphatic instrumentation using the techniques described above. A system in accordance with the invention may have any or all of the components depicted in the figure. A workstation 601 is a computer in communication with the other system components and provides a user interface for controlling the operation of the system. The workstation provides an output for actuating the catheter controller 605 that mechanically pushes a catheter (or guide wire) 651 into the lymphatic system of patient 650. The catheter 651 incorporates a lymphatic instrument that can either be used while the catheter is in place or implanted for chronic use. In the latter case, the lymphatic instrument may be either a lead-based instrument attached to an implantable device or a wireless satellite unit. An electro-stimulator 606 and vacuum actuator 607 are also interfaced to the workstation for facilitating passage of the catheter 651 through valves in the lymph vessels. As described above, the electro-stimulator provides electrical energy to an electrode of the catheter 651 in order to cause contraction of smooth muscle in the lymphatic vessel walls and create a pressure gradient to open lymphatic valves. The vacuum actuator 607 draws a vacuum through a lumen of the catheter 651 in order to open lymphatic valves. The system also has the capability for magnetically guiding a ferromagnetic tip of the catheter 651 (or guide wire) by means of movable guiding magnets 611, and a magnet actuator 610 is interfaced to the workstation for this purpose. In order to provide the operator with information as to the location of the catheter within the lymphatic system, a fluoroscope 620 is interfaced to the workstation. When the patient's lymphatic system is injected with a radio-opaque dye through a port of the catheter, the fluoroscope provides images of the lymphatic vessels as the catheter travels therethrough. The workstation is also interfaced to an image repository 630 that stores images of the patient's anatomy obtained with one or more other imaging modalities such as conventional x-ray, CAT, MRI, and ultrasound. The operator may overlap an image from the image repository with the fluoroscopic image in order to provide anatomical landmarks for guiding the catheter to a selected location in the patient's body.

Figure 7:
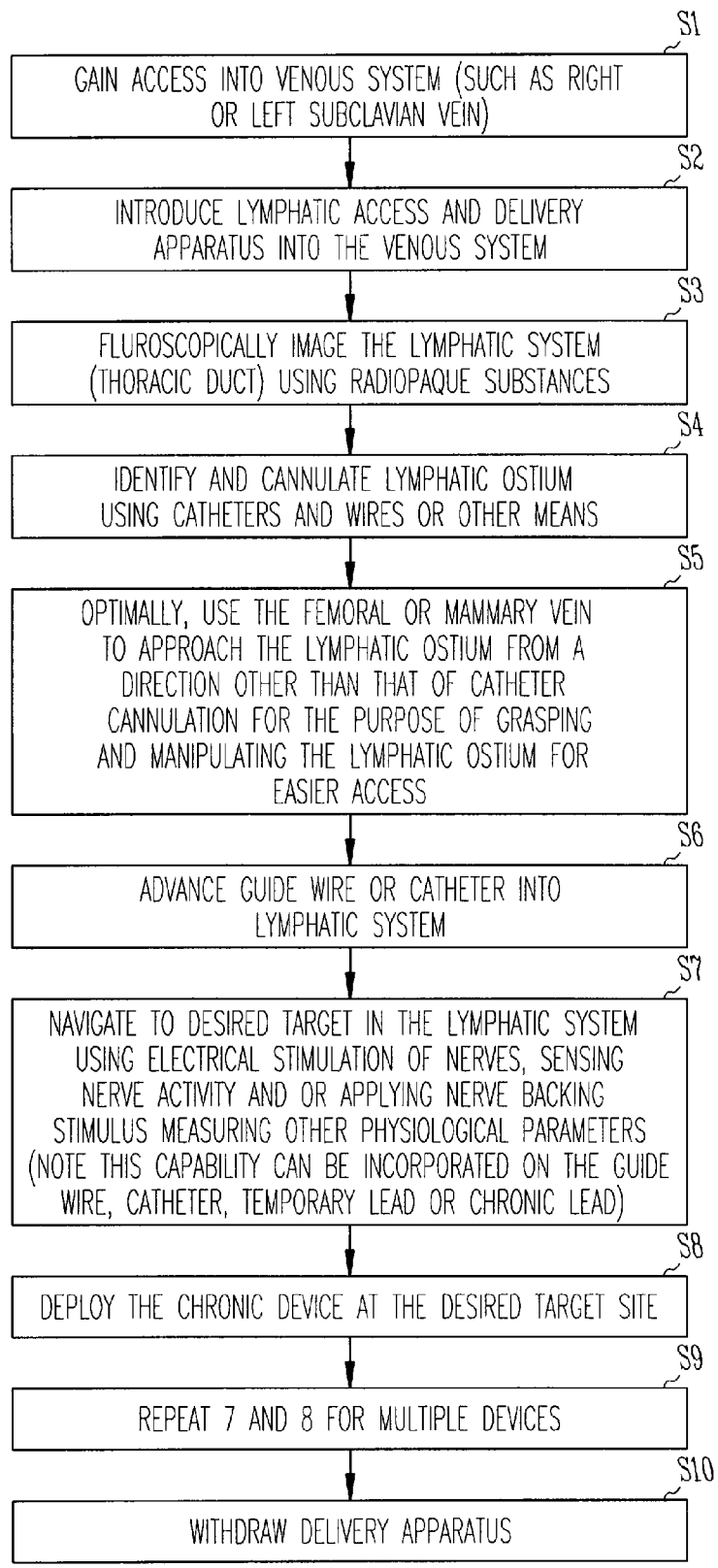
FIG. 7 illustrates exemplary steps for introducing endolymphatic instrumentation into a patient's body.

FIG. 7 is a block diagram that illustrates the steps involved in introducing endolymphatic instrumentation into a patient's body. The technique may be used in situations in which one or more lymphatic instruments are to be chronically implanted or in situations in which the lymphatic instrument is to be used for diagnostic and/or therapeutic purposes and then withdrawn. At step S1, access is gained into venous system (such as right or left subclavian vein) such as by cannulation. At step S2, the lymphatic access and delivery apparatus (e.g., a guide wire or catheter) is introduced into the venous system. At step S3, the lymphatic system is fluoroscopically imaged using radiopaque substances. The lymphatic ostium of the thoracic duct is identified and cannulated using catheters and wires or other means at step S4. When necessary, a technique may be employed at step S5 using the femoral or mammary vein to approach the lymphatic ostium from a direction other than that of catheter cannulation for the purpose of grasping and manipulating the lymphatic ostium for easier access. The guide wire or catheter is advanced into the lymphatic system at step S6. The lymphatic instrument is navigated to desired target in the lymphatic system at step S7 using electrical stimulation of nerves, sensing nerve activity and/or applying nerve blocking stimulus measuring other physiological parameters (this capability can be incorporated on the guide wire, catheter, temporary lead or chronic lead). The instrument is deployed at the desired target site at step S8. At step S9, steps S7 and S8 are repeated if multiple lymphatic instruments are to be implanted on either a chronic or temporary basis. At step S10, the delivery apparatus is withdrawn.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A method, comprising:
   introducing a catheter having a lymphatic instrument incorporated therein into a patient's venous system;
   advancing the catheter through the venous system to reach the thoracic duct;
   advancing the catheter through the thoracic duct into a lymphatic vessel;
   fluoroscopically imaging the patient's lymphatic vessel as the lymphatic instrument is guided therethrough;
   opening lymphatic valves by drawing a vacuum through a lumen of the catheter in order to create a negative pressure gradient within the lymphatic vessel;
   simultaneously pushing the catheter through the lymphatic valves as they are opened by the negative pressure gradient; and
   positioning the lymphatic instrument at a selected location within the patient's lymphatic vessel to deliver therapy or sense one or more physiological variables.

2. The method of claim 1 further comprising introducing the lymphatic instrument by means of a guide wire.

3. The method of claim 1 further comprising implanting an implantable control device that communicates with the lymphatic instrument.

4. The method of claim 3 wherein the lymphatic instrument is incorporated into a lead adapted for connecting to the implantable control device.

5. The method of claim 1 wherein the lymphatic instrument is incorporated into a satellite unit that wirelessly communicates with an implantable or external control device.

6. The method of claim 5 further comprising implanting a stent incorporating the satellite unit with the catheter.

7. The method of claim 1 further comprising navigating the lymphatic instrument to the target location by delivering an electrical stimulus to nerves and sensing nerve activity.

8. The method of claim 1 further comprising employing an electro-stimulator incorporated into the catheter to open lymphatic valves in order to facilitate the passage of the catheter therethrough.

9. The method of claim 1 further comprising employing an inflatable balloon incorporated into the catheter to open lymphatic valves in order to facilitate the passage of the catheter therethrough.

10. The method of claim 1 further comprising employing one or more guide magnets and a catheter or guide wire with a ferromagnetic tip to guide the lymphatic instrument through the lymphatic system.

11. The method of claim 1 further comprising overlapping a fluoroscopic image with an anatomical image of the patient's body to facilitate placement of the lymphatic instrument at a selected location.

12. The method of claim 1 further comprising cannulating the lymphatic ostium of the patient's thoracic duct, and guiding the lymphatic instrument through the thoracic duct to a selected target location.

13. The method of claim 12 further comprising assisting initial cannulation of the lymphatic ostium by use of an endovascular grasping instrument for manipulating the lymphatic ostium.

14. The method of claim 13 further comprising introducing the endovascular grasping instrument through the femoral or mammary vein of the patient.

15. A system for introducing endolymphatic instrumentation, comprising:

a stent incorporating a lymphatic instrument configured to measure a physiological variable and that is configured to communicate wirelessly with an external or implantable device;
a catheter configured to implant the stent;
a catheter controller configured to mechanically push the catheter into the lymphatic system of a patient;
a vacuum actuator configured to draw a vacuum through a lumen of the catheter in order to create a pressure gradient within a lymphatic vessel and open lymphatic valves as the catheter is pushed therethrough by the catheter controller;
wherein the system is configured to operate the catheter controller to simultaneously push the catheter as vacuum is drawn through the lumen of the catheter; and,
a workstation that provides a user interface configured to control operation of the system and which provides an output configured to actuate the catheter controller and vacuum actuator.

16. The system of claim 15 further comprising an electro-stimulator for providing electrical energy to an electrode of the catheter in order to cause contraction of smooth muscle in the walls of the lymphatic vessel and create a pressure gradient to open lymphatic valves.

17. The system of claim 15 further comprising:
a ferromagnetic tip of the catheter;
movable guiding magnets for magnetically guiding the tip of the catheter; and,
a magnet actuator interfaced to the workstation actuating the guiding magnets.

18. The system of claim 15 further comprising a fluoroscope is interfaced to the workstation configured to produce a fluoroscopic image of the patient.

19. The system of claim 18 further comprising an image repository interfaced to the workstation that stores anatomical images of the patient obtained with one or more other imaging modalities such as conventional x-ray, CAT, MRI, and ultrasound and which allows an operator to overlap an anatomical image from the image repository with the fluoroscopic image in order to provide anatomical landmarks for guiding the catheter to a selected location.

* * * * *